United States Patent [19]

Buckland

[11] Patent Number: 5,212,318
[45] Date of Patent: May 18, 1993

[54] PREPARATION OF OMEGA-SUBSTITUTED ALKANAMIDE

[75] Inventor: Paul R. Buckland, Pittsford, N.Y.

[73] Assignee: Eastman Kodak Company, Rochester, N.Y.

[21] Appl. No.: 663,525

[22] Filed: Mar. 4, 1991

[51] Int. Cl.$^5$ .................. C07D 233/84; C07D 405/12
[52] U.S. Cl. .............................. 548/315.7; 548/324.1
[58] Field of Search ................. 548/336, 337, 315.7, 548/324.1

[56] References Cited

U.S. PATENT DOCUMENTS

| | | | |
|---|---|---|---|
| 3,271,451 | 9/1966 | Tushler et al. | 564/377 |
| 3,536,721 | 10/1970 | Soong et al. | 546/245 |
| 3,715,363 | 2/1973 | Dickman | 548/165 |

FOREIGN PATENT DOCUMENTS 372445 6/1990 European Pat. Off.
11609 6/1965 Japan.

OTHER PUBLICATIONS

Kita et al., Chem. Pharm. Bull., 38 (6) 1473–1478 (1990).

*Primary Examiner*—Mary C. Lee
*Assistant Examiner*—Lenora Ava Miltenberger

[57] ABSTRACT

A method for the preparation of omega-arylthioalkanamides, especially omega-imidazolylthioalkanamides useful, for example, in the preparation of certain antihypercholesterolemic agents is disclosed. The method involves three steps including an addition reaction between a lactone and an amine to produce an omega-hydroxyalkanamide; a condensation reaction between said omega-hydroxyalkanamide and an alkanesulfonic acid halide or anhydride to produce an alkanesulfonate ester; reaction of said alkanesulfonate ester with a salt of an aromatic mercaptan, especially an imidazole-2-thiol, to produce the omega-imidazolylthioalkanamides.

3 Claims, No Drawings

PREPARATION OF OMEGA-SUBSTITUTED ALKANAMIDE

CROSS-REFERENCE TO RELATED APPLICATIONS

Reference is made to the following copending and commonly assigned applications: U.S. Ser. No. 07/664,157 filed on Mar. 4, 1991, now abandoned, by Paul R. Buckland, entitled "Sulfonate Ester".

FIELD OF THE INVENTION

This invention relates to substituted imidazoles useful in the preparation of antihypercholesterolemic agents used in treating atherosclerosis and in lowering serum cholesterol.

BACKGROUND OF THE INVENTION

The synthesis and use of substituted imidazoles in pharmaceutical preparations useful in treating atherosclerosis and in lowering serum cholesterol has been disclosed. For example, EP 0 372 445 A1 discloses an antihypercholesterolemic agent having the formula:

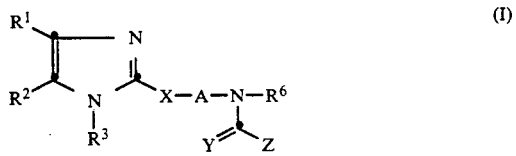

wherein the substituents (R1, R2, R3, R6, A, X, Y, and Z) are as disclosed therein for Formula (I). (See EP 0 372 445 A1, pp. 5–7).

Scheme 1, disclosed on page 9 of the European application, utilizes an imidazole as the starting compound and produces the antihypercholesterolemic agent as follows:

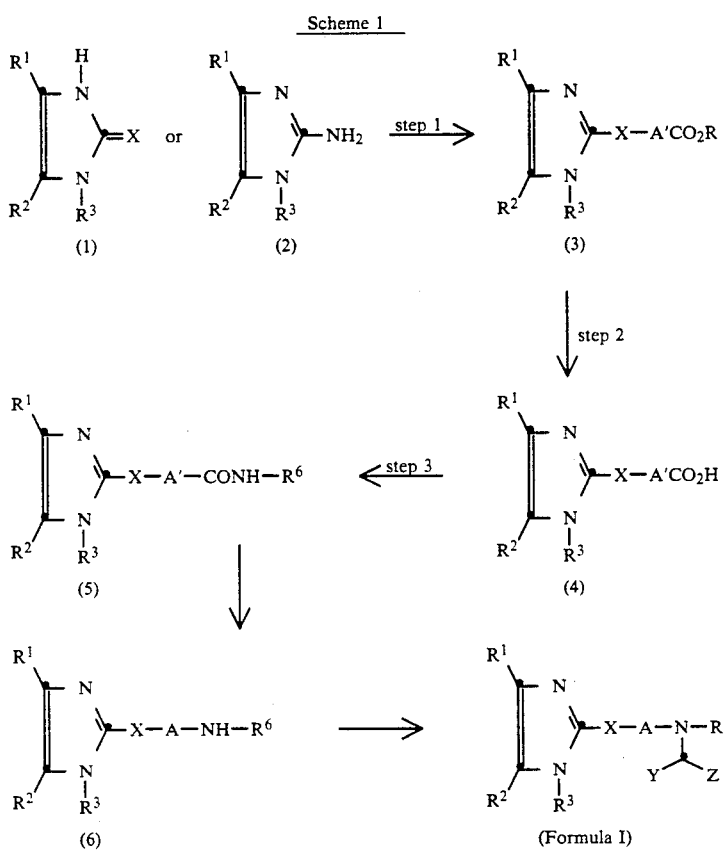

wherein the substituents are as defined for Formula (I).

According to the scheme presented above, the esters of Formula (3) are hydrolyzed to the corresponding carboxylic acids of Formula (4) by methods well known in the art. The amides of Formula (5) are prepared by coupling the carboxylic acids of Formula (4) with a primary amine by amide bond forming reactions known in the art.

The problem is that the process represented by this reaction scheme is expensive because it is protracted and requires expensive omega-haloalkanoates such as ethyl 5-bromopentanoate (step 1). Furthermore, the use of omega-haloalkanoates at the outset of a multistep synthesis, increases the cost disadvantage of this process. A further disadvantage to the use of omega-haloalkanoates is that many are lachrymators and/or irritants. Yet another disadvantage is that step 3 needs expensive dehydrating agents or requires two reaction steps via the acid chloride. Finally, as shown in the examples of the European application, the overall yield of the compound of Formula (5) is only modest. The compound of Formula (5) is similar to the final product of the present invention.

The European application also describes an alternative reaction (Scheme 4) for preparing the amides of Formula (5) which in turn are used to prepare compounds of Formula (I). Alternative Scheme 4 is represented in the European application (p. 11) as follows:

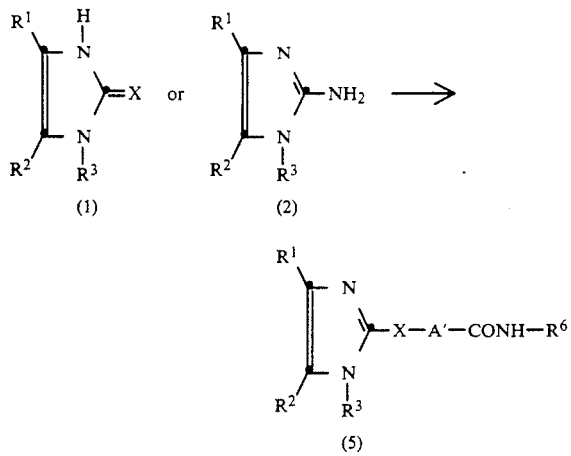

wherein the substituents are as described for Formula (I).

Without teaching how, EP 0 372 445 A1 suggests that alternatively the amides of Formula (5) can be prepared by the alkylation of Formula (1) or (2) with compounds of the formula:

wherein M is a halogen or tosylate group; A' is a moiety having one less methylene group than A (as described for Formula (I); and $R^6$ is as defined for Formula (I).

The European application merely alludes to this alternative alkylation step. It does not teach the preparation of M—(A')CONHR$^6$ (designated compound II), nor does it indicate the efficiency, yield, or economy of the suggested alkylating compound II, M—(A')-CONHR$^6$.

We have found that tosylate esters of this formula (wherein M=tosylate group) decompose at ambient temperatures or more rapidly on heating. The comparative example herein shows that formation of the suggested tosylate esters of compound II occurs only slowly at room temperature. During the slow reaction at room temperature, the product begins to decompose even before the reaction is complete, thus yielding less than optimum amounts of product.

We have also found that the tosylate esters are difficult to purify and difficult to solidify. On the other hand, although the halogen compounds of Formula II (wherein M=halogen) can be derived from omega-haloalkanoyl chlorides, these materials are expensive to produce and many are lachrymators. Furthermore, the chloro analogs alkylate only slowly and incompletely.

What is needed to produce a high overall yield of compounds of formula (5) are reactive alkylating agents which are themselves rapidly formed and are capable of being obtained pure from inexpensive and readily available starting materials.

SUMMARY OF THE INVENTION

We have developed a general process for the preparation of the omega-arylthioalkanamides of Formula (5) especially omega-imidazolylthioalkanamides, compounds useful, for example, in the preparation of certain antihypercholesterolemic agents. More specifically, this process comprises the steps of:

(a) adding a 5 to 7 membered ring lactone to an amine to produce an omega-hydroxyalkanamide;

(b) condensing the omega-hydroxyalkanamide of step (a) with an alkanesulfonic acid halide or anhydride to produce an alkanesulfonate ester; and (c) alkylating the salt of an aromatic mercaptan, for example an imidazole-2-thiol, with the alkanesulfonate ester produced in step (b) to produce an arylthioalkanamide.

An advantageous feature of this process is that it utilizes as the starting compound lactones which are readily available, inexpensive, non-toxic compounds capable of being rapidly transformed in high yield to omega-hydroxyalkanamides.

Another advantageous feature of this process is that it utilizes the hydroxy compounds to prepare alkanesulfonate esters, which in contrast to the tosylates are formed rapidly and in high yield at low to ambient temperatures. Furthermore, the alkanesulfonates can be obtained pure without difficulty, in contrast to the tosylates, and are excellent alkylating agents for the preparation of the imidazolylthioalkanamides.

Yet another feature of the invention is that the imidazole-2-thiols can be prepared rapidly and in high yield by using N,N-dimethylformamide as a joint reaction and crystallization solvent in the condensation of a benzoin with ammonium thiocyanate. Use of dioxane (see Bull. Soc. Chim. Belg. 1961, 70, 745) is potentially hazardous, results in longer reaction times and requires additional purification of the product from acetic acid.

Another advantage of this invention is that it avoids the use of lachrymatory materials.

Yet another advantageous feature of the invention is that the final product is provided conveniently and in high overall yield.

DESCRIPTION OF THE PREFERRED EMBODIMENTS

The method of the instant invention may be illustrated generally as follows.

An omega-substituted arylthioalkanamide, such as an omega-substituted imidazolylthioalkanamide, having the structure:

$$ArS—Y—CONR^8R^9$$

is prepared by the following steps:

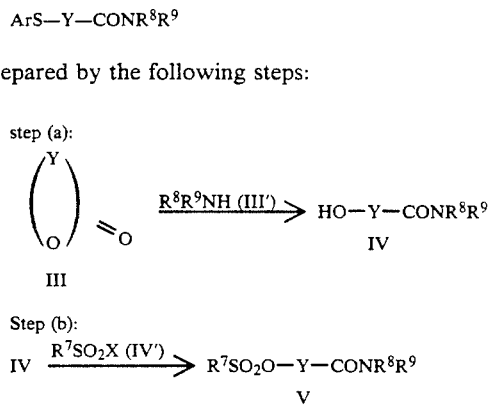

wherein (III) is a 5, 6, or 7 membered ring lactone such as delta valerolactone,
(III') is an amine,
(IV) is an omega-hydroxyalkanamide,
(IV') is an alkanesulfonic acid halide or anhydride,
(V) is an omega-alkanesulfonoxyalkanamide,
(VI) is an omega-substituted arylthioalkanamide such as an omega-imidazolylthioalkanamide,
$R^7$ is selected from the group consisting of substituted or unsubstituted lower alkyls of 1-4 carbon atoms such as methyl, trifluoromethyl, ethyl, propyl, isopropyl.
$R^8$ and $R^9$ each independently represents hydrogen, alkyl, alkenyl, cyclic alkyl, cyclic alkenyl, phenyl optionally substituted with 1 to 3 groups selected from $C_1$-$C_4$ alkyl or alkoxy, F, Br, Cl, OH, CN, $CO_2H$, $CF_3$, $NO_2$, $C_1$-$C_4$ carboalkoxy, $NR^{10}R^{10}$, or $NCOR^{11}$, benzyl optionally substituted with 1 to 3 groups selected from $C_1$-$C_4$ alkyl or alkoxy, F, Br, Cl, OH, CN, $CO_2H$, $CF_3$, $NO_2$, $C_1$-$C_4$ carboalkoxy, $NR^{10}R^{10}$, or $NCOR^{11}$, furfuryl, alkoxyalkyl and cyclic alkyl ethers with the proviso that $R^8$ and $R^9$ cannot both be aromatic. The term "cyclic alkyl" means a radical such as cyclohexyl which may be attached at the $R^8$ and/or $R^9$ position.
$R^{10}$ is selected independently from $C_1$ to $C_4$ alkyl.
$R^{11}$ is selected independently from H or $C_1$ to $C_4$ alkyl.
Y is selected from the group consisting of unsubstituted or substituted trimethylene, tetramethylene or pentamethylene, exemplary substituents being lower alkyl such as methyl, ethyl, propyl or butyl.
Ar is phenyl, naphthyl, or 4,5-disubstituted-1H-imidazol-2-yl.
By "hetero" is meant an atom other than carbon, C, in the aromatic ring, especially O, S, and N atoms.
X is an acid anion, preferably selected from the group consisting of F, Cl, Br.
The term "omega", as used herein, refers to the terminal or highest number position. It can be the 4, 5, or 6 position regardless of whether there are alkyl substituents at that same position.
More specifically, the omega-arylthioalkanamide is produced by the following steps.

Step (a): Addition Reaction

A lactone is reacted with an amine to produce an omega-hydroxyalkanamide. Preferably, the lactone has 5, 6, or 7 carbon atoms because these lactones are the most readily available and least expensive.
The following lactones are among those which would be useful in this reaction:
gamma-butyrolactone, gamma valerolactone, delta-valerolactone, gamma-caprolactone, epsilon-caprolactone.
Useful amines include n-heptylamine and aniline as well as other aliphatic and aromatic primary and secondary amines.
The lactone and amine are made to react without a solvent as, unexpectedly, we have obtained a better yield in 3 to 6 hours under these conditions. The reaction takes place slowly at room temperature or more rapidly at elevated temperatures of about 40°-150° C., preferably 80°-110° C. The resulting omega-hydroxyalkanamide may be recovered after crystallization as a solid or, to save time and for greater convenience, it may be reacted in situ during step (b).

Step (b): Condensation Reaction

The hydroxyalkanamide resulting from step (a) is condensed with a small excess (about 5 to 10%) of methanesulfonic acid halide or anhydride in the presence of a small excess (about 10 to 20%) of an acid scavenger, for example, a tertiary amine such as triethylamine and the like. Suitable solvents are dichloromethane, methyl ethyl ketone, tetrahydrofuran, ethyl acetate and N,N-dimethylformamide. An inexpensive and readily available sulfonyl halide such as methanesulfonyl chloride is preferred. The reaction is carried out preferably between 10° C. and room temperature. The resulting sulfonate ester is recovered after crystallization as a solid or reacted in situ in step (c).
Again, the ability of the product to react in situ in the next step is both time-saving and convenient. Unexpectedly, the alkanesulfonate ester formed as an intermediate in the presently claimed process, can be readily recovered as a white solid with a 92% yield. This result is unexpected in view of our finding that the yield of the tosyl ester is only 76% and the product is difficult to purify. (See comparative example).

Step (c): Alkylation

An aromatic mercaptan such as 4,5-diphenyl-1H-imidazole-2-thiol is heated to about 50° C. in dimethylformamide (DMF) until the thiol dissolves, after which a non-nucleophilic base such as potassium carbonate is added. 4,5-diphenyl-1H-imidazole-2-thiols are preferred because they can be prepared rapidly and in high yield by contacting a benzoin with ammonium thiocyanate in the presence of N,N-dimethylformamide as joint reaction and crystallization solvent. The preferred method of preparation is disclosed in the Example below. The sulfonate ester of step (b) is added in portions over 4 hours and the mixture rapidly stirred for a further 2 hours preferably at about 50°-55° C. The final product, an omega-substituted imidazolylthioalkanamide is then crystallized, washed and recovered as a white solid.
The following example is given for purposes of illustration and should not be construed as limiting the invention.

EXAMPLE

Preparation of
N-heptyl-5-[(4,5-diphenyl-1H-imidazol-2-yl)thio]pentanamide

Step (a): Preparation of
N-Heptyl-5-hydroxypentanamide

Delta valerolactone (40 g, 0.4 mole) was added dropwise with stirring to n-heptylamine (50.6 g, 0.4 mole) so that the temperature of the mixture was maintained at 85° to 90° C. Heat was applied and the temperature raised to 110° C. over 20 minutes after which the temperature was maintained at 110° to 115° C. for a further 6 hours (after 3 hours N.M.R. indicated that the reaction was 90 to 95% complete). Toluene (200 ml, 173 g) was added and the solution cooled to 0° C. with stirring. After 1 hour at 0° C., the solid was collected and washed successively with ice cold toluene (50 ml, 43 g) and n-heptane (50 ml, 34 g). The material was dried at room temperature overnight to give the product. (81.6 g (95% yield) m.p. 53° to 54° C.).
The reaction is represented as follows:

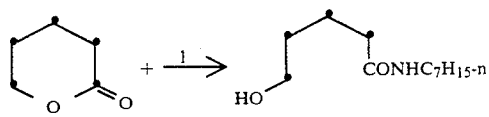

C$_5$H$_8$O$_2$
M.W. 100
delta valero-
lactone

C$_{12}$H$_{25}$NO$_2$
M.W. 215
N-heptyl-5-
hydroxypent-
anamide 1. n-heptylamine, heat from 110 to 115° C. for 6 hours.

Step (b): Preparation of N-heptyl-5-methanesulfonoxypentanamide

Dichloromethane (70 ml, 93 g) was added to a 4 necked 500 ml flask (condenser/drying tube, dropping funnel, thermometer, overhead stirrer) containing N-heptyl-5-hydroxypentanamide (32.25 g, 0.15 mole). Cooling occurred as the solid partially dissolved. Methanesulfonyl chloride (18.0 g, 0.1575 mole, 5% excess) was added and stirring continued at 15° C. for 30 minutes during which most of the solid dissolved. Cooling below 15° C. at this stage is not recommended because a thick slurry is produced due to recrystallization of the starting material. Dropwise addition over 1 hour, of a mixture of triethylamine (16.66 g, 0.165 mole, 10% excess) and dichloromethane (30 ml, 40 g) was commenced with cooling, so that the temperature remained at 13° to 16° C. throughout the addition. Shortly after (about 10 minutes), the addition was complete, t.l.c. (ethyl acetate, iodine/warm plate) indicated absence of starting material. After a further 1 hour, the mixture was stirred rapidly with cold 10° C. water (50 ml) for 1 minute. The layers were allowed to separate out over a further 5 minutes and the top aqueous layer (50 ml) carefully siphoned off and discarded. The washing procedure was repeated using cold (10° C.) 15% sodium chloride solution (40 ml) removing the top layer (35 ml). Finally the mixture was again washed with cold 15% sodium chloride solution (40 ml), this time running off the bottom dichloromethane layer into a 500 ml flask containing sodium sulfate (35 g). After stirring for 15 minutes at 15° C., the mixture was filtered through anhydrous sodium sulfate (35 g) and the residue washed with dichloromethane (50 ml, 66 g). The combined filtrates were evaporated below 20° C. at reduced pressure until crystallization began, to give a semi-solid (94 g). n-heptane (100 ml, 68 g) was added and the mixture gradually cooled to 0° C. After stirring at 0° C. for 1 hour, the solid (47 g) was collected, washed with n-heptane (25 ml, 17 g) and dried at room temperature to give the product 40.7 g (92% yield) as a white solid, m.p. 63° to 64° C.

The reaction is represented as follows:

C$_{12}$H$_{25}$NO$_2$
M.W. 215
N-heptyl-5-hydroxy-
pentanamide

-continued

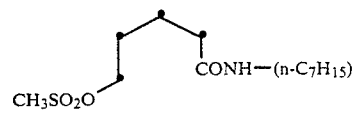

C$_{13}$H$_{27}$NO$_4$S
M.W. 293
N-heptyl-5-methane-
sulfonoxypentanamide

1. Methanesulfonyl chloride, triethylamine, dichloromethane.
2. Crystallize dichloromethane/n-heptane.

Step (c): Preparation of N-heptyl-5-[(4,5-diphenyl-1H-imidazol-2-yl)thio]pentanamide Preparation of 4,5-diphenyl-1H-imidazole-2-thiol:

Ammonium thiocyanate (228 g, 3 mole) and N,N-dimethylformamide (DMF) (500 mL), were stirred and heated to 115° C. Benzoin (212 g, 1 mole) in hot DMF (500 mL) was added dropwise maintaining the temperature between 115° to 120° C. After addition was complete, the temperature was kept at 115° to 120° C. for a further 1 hour. The mixture was cooled to 25° C. over a further 1 hour. The crystalline material was collected and washed successively with methanol (3×100 mL, 3×79 g), H$_2$O (3×100 g) and again with MeOH (3×100 mL, 3×79 g). The off-white solid was dried at 60° C. to give the product 203.8 g (81% yield).

N,N-dimethylformamide (DMF) (from previously unopened bottle, 300 ml, 283 g) was heated to 55° C. in a 1 liter 4 necked vessel (thermometer, condenser/drying tube, overhead stirrer). Powdered 4,5-diphenyl-1H-imidazole-2-thiol as described above, (28.35 g, 0.1125 mole) was added in portions with stirring and the thiol allowed to dissolve over a further 30 minutes. Anhydrous potassium carbonate (25.5 g, 0.185 mole) was finely ground and the resulting hydroscopic material added quickly. Stirring was continued for a further 30 minutes. In the meantime, N-heptyl-5-methylsulfonoxypentanamide (4×9.15 g, 0.125 mole, 10% excess) was weighed into four separate bottles. A portion (9.15 g) of the sulfonate ester was added to the rapidly stirred mixture and stirring continued at 50° to 55° C. for 1 hour. The addition procedure for the sulfonate ester was repeated a further three times. T.l.c. (ethylacetate) after 4 hours showed the presence of a little unreacted thiol. The mixture was stirred at 50° to 55° C. for a further 2 hours and then cooled to 30° C. Toluene (160 ml, 139 g) and then water (150 g) were added and the mixture rapidly stirred for 5 minutes. The layers were allowed to separate and the bottom aqueous layer run off and discarded. The upper toluene layer was washed successively with 5% aqueous potassium carbonate (2×200 g) and water (200 g). The wet toluene solution was heated to 50° C. and the solvent removed under reduced pressure to give an orange oil (70 g). Hot (70° C.) acetonitrile (400 ml, 314 g) was added with stirring and the solution allowed to cool to 45° C. The mixture was kept at 45° C. with stirring overnight and then cooled to 30° C. The solid was collected, washed with acetonitrile (100 ml, 80 g) and dried at 60° C. for 24 hours to give the product as a white solid 36.7 g (73% yield), m.p. 103.5° to 104.5° C. one spot t.l.c. (ethyl acetate).

The reaction is represented as follows:

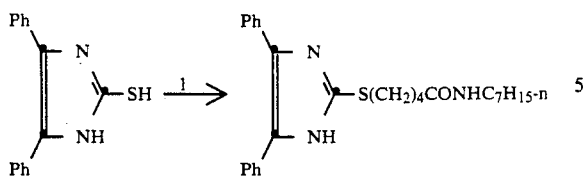

4,5-Diphenyl-1H-imidazole-2-thiol
$C_{15}H_{12}N_2S$
M.W. 252

N-heptyl-5-[(4,5-diphenyl-1H-imidazol-2-yl)thio]pentanamide
$C_{27}H_{35}N_3OS$
M.W. 449

1. N-heptyl-5-methylsulfonoxypentanamide $(C_{13}H_{27}NO_4S)$, $K_2CO_3$, DMF.

COMPARATIVE EXAMPLE

Comparative-Preparation of N-heptyl-5-tosyloxypentanamide

N-heptyl-5-hydroxypentanamide (3.23 g, 0.015 mole) and tosyl chloride (3.0 g, 0.1575 mole) were dissolved at room temperature in dichloromethane (10 ml). Cooling occurred as the solids dissolved. When complete solution was obtained (10 minutes), triethylamine (1.66 g, 0.0165 mole) was added dropwise at 16° C. No exotherm occurred. The temperature was maintained at 15° to 17° C. for a further 2 hours. The mixture was then washed successively with ice cold water (2×5 ml) and finally with saturated sodium chloride solution (5 ml). The organic solution was dried with sodium and magnesium sulfates and the solvent removed at room temperature to give a yellow oil 6.2 g. An N.M.R. spectrum indicated a 76% conversion of alcohol to sulfonate ester (product:alcohol 3.2:1). The oil did not crystallize at ambient temperatures but crystallized at −20° C. from toluene (10 ml) and n-heptane (5 ml) to give a solid 2.8 g which was still contaminated with unreacted alcohol (product:alcohol 2.8:1). This crude material was readily soluble in all common organic solvents except alkanes.

Despite the use of excess tosyl chloride, the initial 76% yield of sulfonate ester did not improve. Very little if any further conversion of alcohol occurred at longer reaction times up to 48 hours. After 48 hours N.M.R. showed unreacted alcohol still present and also confirmed that substantial decomposition of the product occurs on keeping in solution at ambient temperatures.

The reaction is represented as follows:

$C_{12}H_{25}NO_2$
M.W. 215

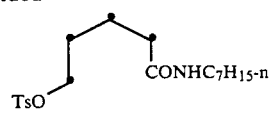

$C_{19}H_{31}NO_4S$
M.W. 369

1. Tosylchloride, triethylamine, dichloromethane.
2. Crystallize from toluene/n-heptane.

The invention has been described in detail with particular reference to preferred embodiments thereof, but it will be understood that variations and modifications can be effected within the spirit and scope of the invention.

I claim:

1. A process for preparing an omega-substituted arylthioalkanamide of the formula $$ArS—Y—CONR^8R^9,$$

wherein

Ar is 4,5-diphenyl-1H-imidazol-2-yl;

Y is selected from the group consisting of trimethylene, tetramethylene, or pentamethylene, or trimethylene, tetramethylene, or pentamethylene substituted by a group selected from the list consisting of methyl, ethyl, propyl, or butyl;

$R^8$ and $R^9$ each independently represents hydrogen, $C_1$-$C_7$ alkyl, phenyl optionally substituted with 1-3 groups selected from $C_1$-$C_4$ alkyl or alkoxy, F, Br, OH, CN, $CO_2H$, $CF_3$, $NO_2$, $C_1$-$C_4$ carbalkoxy, $NR^{10}R^{10}$, $NCOR^{11}$, and furfuryl, with the proviso that $R^8$ and $R^9$ cannot both be aromatic;

$R^{10}$ is $C_1$-$C_4$ alkyl; and $R^{11}$ is H or $C_1$-$C_4$ alkyl;

which comprises the steps:

(a) reacting delta valerolactone with an amine of the formula $R^8R^9NH$, to provide a compound of the formula $$HO—Y—CONR^8R^9;$$

followed by (b) treatment with a compound of the formula $R^7SO_2X$, wherein $R^7$ is a lower alkyl group of 1-4 carbon atoms, or trifluoromethyl; and X is an anion selected from the group consisting of —F, —Cl, and —Br; to provide a compound of the formula $$R^7SO_2O—Y—CONR^8R^9;$$

followed by (c) treatment with a compound of the formula ArSH in the presence of a non-nucleophilic base.

2. The process of claim 1, wherein the amine of formula $R^8R^9NH$ is n-heptylamine.

3. The process of claim 2, wherein $R^7$ is methyl and X is chloro.

* * * * *